US00PP23259P2

(12) United States Plant Patent
Burton

(10) Patent No.: US PP23,259 P2
(45) Date of Patent: Dec. 18, 2012

(54) ***COPROSMA* PLANT NAMED 'MIDNIGHT MARTINI'**

(50) Latin Name: *Coprosma repens*
Varietal Denomination: Midnight Martini

(76) Inventor: Stephen Burton, Cambridge (NZ)

( * ) Notice: Subject to any disclaimer, the term of this patent is extended or adjusted under 35 U.S.C. 154(b) by 0 days.

(21) Appl. No.: 13/136,513

(22) Filed: Aug. 3, 2011

(51) Int. Cl.
*A01H 5/00* (2006.01)

(52) U.S. Cl. ..... Plt./226

(58) Field of Classification Search ..... Plt./226, Plt./263.1
See application file for complete search history.

(56) References Cited

PUBLICATIONS http://www.ballhort.com/Nursery/plant_info.aspx?phid=01870124802697 (*Coprosma* 'Martini Midnight').*
Pluto: Plant Variety Database, citation for 'Midnight Martini'.*

* cited by examiner

*Primary Examiner* — Howard Locker
(74) *Attorney, Agent, or Firm* — Mark P. Bourgeois

(57) ABSTRACT

A new cultivar of *Coprosma* plant named 'Midnight Martini' that is characterized by a compact habit and leaves that are green with center yellow streaks and a dark bronze margin.

1 Drawing Sheet

Botanical classification: *Coprosma repens.*
Variety denomination: 'Midnight Martini'.

BACKGROUND OF THE INVENTION

The present invention relates to a new and distinct cultivar of *Coprosma* plant botanically known as *Coprosma repens* and hereinafter referred to by the cultivar name to 'Midnight Martini'.

The new cultivar was discovered as a naturally occurring branch mutation of *Coprosma* 'Tequila Sunrise' (U.S. Plant Pat. No. 18,392). 'Midnight Martini' was discovered in a cultivated area of Cambridge, New Zealand in 2007.

Asexual reproduction by tip cuttings of the new cultivar 'Midnight Martini' was first performed in 2007 in Cambridge, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Midnight Martini'.

1. *Coprosma* 'Midnight Martini' exhibits a compact habit.
2. *Coprosma* 'Midnight Martini' exhibits leaves that are green with center yellow streaks and a dark bronze margin.

The closest comparison cultivar is the parent plant *Coprosma* 'Tequila Sunrise'. The new cultivar 'Midnight Martini' is distinguishable from 'Tequila Sunrise' by the following characteristics:

1. 'Midnight Martini' has leaves that are green with center yellow streaks and a dark bronze margin. The leaves of 'Tequila Sunrise' have margins that are lighter red in color.

BRIEF DESCRIPTION OF THE DRAWING

The accompanying photograph illustrates the distinguishing traits of *Coprosma* 'Midnight Martini'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Midnight Martini'. Data was collected in Cambridge, New Zealand from 12 month old outdoor grown plants in 2.5 liter containers. The time of year was Fall in the Southern Hemisphere and the average temperature range was 18 to 25 degrees Centigrade during the day and 12 to 20 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species and include well drained soils with partial to full sun. 'Midnight Martini' has not been tested under all possible conditions and phenotypic differences may be observed with variations in environmental, climatic, and cultural conditions, however, without any variance in genotype.

Botanical classification: *Coprosma repens* 'Midnight Martini'.
Use: Ornamental perennial.
Parentage: 'Midnight Martini' is a naturally occurring branch mutation of *Coprosma* 'Tequila Sunrise'.
Vigor: Moderate.
Growth rule: Moderate.
Growth habit: Freely branching, dense, bushy habit.
Plant shape: Broad upright inverted triangle.
Suitable container size: 2.5 liter container.
Height: Average 1.0 m in height.
Width: Average 1.0 m in width.
Hardiness: Tolerant to −3 degrees Centigrade.
Propagation: Tip cuttings.

Time to initiate roots: Approximately 20 days in the Summer and 25 days in the Winter.

Time to produce a rooted cutting: Approximately 40 days in the Summer and 200 days in the Winter.

Root system: Fine and fibrous.

Lateral branches:

*Dimensions*.—18 cm. in length and 3.5 mm. in diameter.

*Quantity*.—Approximately 20.

*Strength*.—Strong.

*Texture*.—Smooth.

*Color*.—195A.

*Fall/winter color*.—162D. Pinching of young plants are required to produce uniform foliage.

Foliage:

*Leaf arrangement*.—Opposite.

*Leaf attachment*.—Sessile.

*Compound or single*.—Single.

*Leaf shape*.—Obovate.

*Leaf apex*.—Obtuse.

*Leaf base*.—Rounded.

*Leaf length*.—Average 3.5 cm in length.

*Leaf width*.—1.7 cm in width.

*Pubescence*.—Absent.

*Leaf margin*.—Entire, slightly wavy.

*Leaf texture*.—Smooth, glossy (both surfaces).

*Vein pattern*.—Pinnate.

*Young leaf color* (*upper surface*).—143C with center streaks 1A and outer margins 175D.

*Young leaf color* (*lower surface*).—143C and outer margins 175D.

*Mature leaf color* (*upper surface*).—143A with center streaks 1A and outer margins 175B.

*Mature leaf color* (*lower surface*).—143A with outer margins 175B.

*Fall/winter leaf color* (*both surfaces*).—200A with center streaks 33A.

*Durability of foliage to stress*.—High.

Flowers: Flowers have not been observed.

Disease and insect resistance: Plants of the new *Coprosma* have not been observed for disease or insect resistance.

The invention claimed is:

1. A new and distinct variety of *Coprosma* plant named 'Midnight Martini' as described and illustrated.

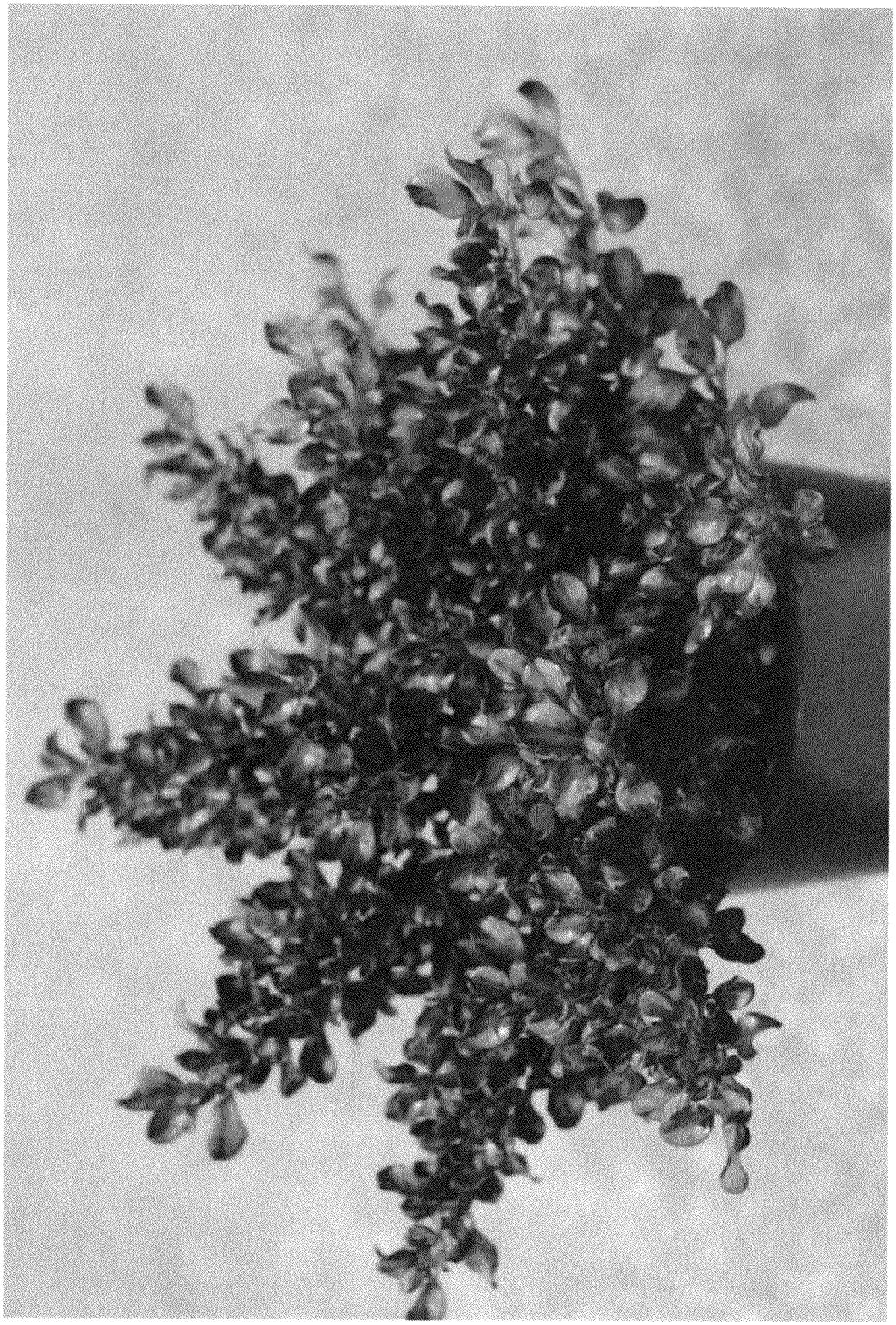

* * * * *